US010881662B2

(12) United States Patent
Kamatani (10) Patent No.: US 10,881,662 B2
(45) Date of Patent: *Jan. 5, 2021

(54) INTRACELLULAR ATP ENHANCER (71) Applicant: StaGen Co., Ltd., Tokyo (JP)

(72) Inventor: Naoyuki Kamatani, Tokyo (JP)

(73) Assignee: STAGEN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/462,345

(22) PCT Filed: Nov. 21, 2017

(86) PCT No.: PCT/JP2017/041733
§ 371 (c)(1),
(2) Date: May 20, 2019

(87) PCT Pub. No.: WO2018/092911
PCT Pub. Date: May 24, 2018

(65) Prior Publication Data
US 2019/0336508 A1 Nov. 7, 2019

(30) Foreign Application Priority Data

Nov. 21, 2016 (JP) ................. 2016-225609
Feb. 23, 2017 (JP) ................. 2017-031953

(51) Int. Cl.
A61K 31/522 (2006.01)
A61K 31/444 (2006.01)
A61K 31/708 (2006.01)

(52) U.S. Cl.
CPC .......... A61K 31/522 (2013.01); A61K 31/444 (2013.01); A61K 31/708 (2013.01)

(58) Field of Classification Search
None
See application file for complete search history.

(56) References Cited

U.S. PATENT DOCUMENTS

| | | | |
|---|---|---|---|
| 8,318,792 | B2 | 11/2012 | Nishino et al. |
| 2003/0059878 | A1 | 3/2003 | Onuki et al. |
| 2006/0293273 | A1 | 12/2006 | Mangano |
| 2011/0257202 | A1 | 10/2011 | Johnson et al. |
| 2015/0272978 | A1 | 10/2015 | Mangano |
| 2017/0216335 | A1 | 8/2017 | Mangano |
| 2018/0243326 | A1 | 8/2018 | Nishino et al. |

FOREIGN PATENT DOCUMENTS

| | | |
|---|---|---|
| JP | 2003-38184 A | 2/2003 |
| JP | 2012-505925 A | 3/2012 |
| JP | 2015-57436 A | 3/2015 |
| WO | WO 2017/033963 A1 | 3/2017 |

OTHER PUBLICATIONS

Crowell, American Journal of Physiology vol. 216, No. 5, Apr. 1969. (Year: 1969).*
Borkowski et al., "Protection of Mouse Heart Against Hypoxic Damage by AMP Deaminase Inhibition," Nucleosides, Nucleotides, and Nucleic Acids (2010), vol. 29, pp. 449-452.
De Jong et al., "Hereditary Spherocytosis and Elliptocytosis Erythrocytes Show a Normal Transbilayer Phospholipid Distribution," Blood (Jul. 1, 1999), vol. 94, No. 1, pp. 319-325.
English translation of International Preliminary Report on Patentability and Written Opinion dated May 31, 2019, in PCT/JP2017/041733 (Forms PCT/IB/388, PCT/IB/373, and PCT/ISA/237).
Gallardo et al., "An α2-Na/K ATPase/α-adducin complex in astrocytes triggers non-cell autonomous neurodegeneration," Nat. Neurosci. (Dec. 2014), vol. 12, pp. 1710-1719.
Glader, B. E., "Salicylate-Induced Injury of Pyruvate-Kinase-Deficient Erythrocytes," N. Engl. J. Med. (Apr. 22, 1976), vol. 294, No. 17, pp. 916-918.
Harmsen et al., "Enhanced ATP and GTP synthesis from hypoxanthine or inosine after myocardial ischemia," Am. J. Physiol. (1984), vol. 246, No. 1, Pt. 2, pp. H37-H43.
Ichida, K., "Febuxostat (TMX-67), Puricase (PEG-Uruicase)," Japanese Journal of Clinical Medicine (2008), vol. 66, No. 4, pp. 759-765.
International Search Report dated Feb. 6, 2018, in PCT/JP2017/041733.
Kurashiro et al., "Xanthine oxidase inhibitor," Heart View (2013), vol. 17, No. 2, pp. 184-186.
Loh et al., "Common Variant in AMPD1 Gene Predicts Improved Clinical Outcome in Patients with Heart Failure," Circulation (1999), vol. 99, pp. 1422-1425.
Markowitz et al.,"The Treatment of Multiple Sclerosis with Inosine," The Journal of Alternative and Complementary Medicine (2009), vol. 15, No. 6, pp. 619-625
McNaughton et al., "Inosine Supplementation Has No Effect on Aerobic or Anaerobic Cycling Performance," International Journal of Sport Nutrition (1999), vol. 9, pp. 333-344.
Mentzer et al., "Hereditary Stomacytosis: Membrane and Metabolism Studies," Blood (Nov. 1975), vol. 46, No. 5, pp. 659-669.
Noman et al.,"Effect of high-dose allopurinol on excercise in patients with chronic stable angina: a randomised, placebo controlled crossover trial," Lancet (2010), vol. 375, pp. 2161-2167.
Norman et al., "Regulation of skeletal muscle ATP catabolism by AMPD1 genotype during sprint exercise in asymptomatic subjects," J. Appl. Physiol. (2001), vol. 91, pp. 258-264.
Ogasawara et al., "Deficiency of AMP deaminase in erythrocytes," Hum. Genet. (1987), vol. 75, pp. 15-18.

(Continued)

Primary Examiner — Layla D Berry
(74) Attorney, Agent, or Firm — Birch, Stewart, Kolasch & Birch, LLP (57) ABSTRACT A problem to be solved by the present invention is to provide a substance having an effect of increasing intracellular ATP and, particular, a potent ATP enhancer far surpassing the increasing effect of inosine alone or a xanthine oxidase/xanthine dehydrogenase inhibitor alone.

A human or animal intracellular ATP enhancer comprising a combination of A) and B):

A) a xanthine oxidase/xanthine dehydrogenase inhibitor; and

B) hypoxanthine, or a compound capable of being converted to hypoxanthine in the body.

11 Claims, 6 Drawing Sheets (56) References Cited

OTHER PUBLICATIONS

Ohtake et al., "Effect of combined use of ATP and allopurinol for ischemic and reperfusion cellular injury," Cyto-protection Biol. (1988), vol. 6, pp. 393-399.

Ohtake et al., "The efficacy of ATP and allopurinol (AL) pretreatment against hypothermic ischemia-reperfusion injury of liver," The Japan Society of Hepatology (1989), vol. 30, No. 4, pp. 444-449.

Opie., L. H., "Allopurinol for Heart Failure," Journal of the American College of Cardiology (2012), vol. 59, No. 9, pp. 809-812.

Palek et al., "Crosslinking of the Nearest Membrane Protein Neighbors in ATP Depleted, Calcium Enriched and Irreversibly Sickled Red Cells," Prog. Clin. Biol. Res. (1978), vol. 20, pp. 75-88.

Sattui, S. E. and A. L. Gaffo, "Treatment of hyperuricemia in gout: current therapeutic options, latest developments and clinical implications," Ther. Adv. Musculoskel. Dis. (2016), vol. 8, No. 4, pp. 145-159.

Schwarzschild et al., The Parkinson Study Group, SURE-PD Investigators, "Inosine to increase serum and CSF urate in Parkinson disease: A randomized, placebo-controlled trial," JAMA Neurol. (Feb. 1, 2014), vol. 71, No. 2, pp. 141-150.

Settle et al., "Effect of Allopurinol and Inosine Administration on Xanthine Oxidoreductase Gene Expression in Selected Tissues of Broiler Chickens," International Journal of Poultry Science (2015), vol. 14, No. 1, pp. 37-43.

Vogt et al., "Lactate accumulation rather than ATP depletion predicts ischemic myocardial necrosis Implications for the development of lethal myocardial injury," Biochimica et Biophysica Acta (2001), vol. 1586, pp. 219-226.

Wang et al., "Allopurinol preserves myocardial energy metabolism in chronic heart failure rats," Journal of Clinical Cardiology (2015), vol. 31, No. 1, pp. 89-93.

Wiley, J. S., "Increased Erythrocyte Cation Permeability in Thalassemia and Conditions of Marrow Stress," J. Clin Invest. (Apr. 1981), vol. 67, pp. 917-922.

Japanese Office Action dated Sep. 2, 2020 for Application No. 2017-031953, along with an English machine translation.

Dua et al., "Acute kidney injury observed during phase 1 clinical trials of a novel xanthine oxidase/URAT1 dual inhibitor PF-06743649," Clin Rheumatol, vol. 35, 2016 (published online Apr. 19, 2016), pp. 2045-2051.

Extended European Search Report for European Application No. 17871969.6, dated Jun. 3, 2020.

Kamatani et al., "Treatment of two mitochondrial disease patients with a combination of febuxostat and inosine that enhances cellular ATP," Journal of Human Genetics, vol. 64, 2019 (published online Jan. 10, 2019), pp. 351-353.

* cited by examiner

| SUBJECT ID | 2 | 3 | 4 | 5 | 6 | 7 | 8 | 9 | 10 |
|---|---|---|---|---|---|---|---|---|---|
| | | GROUP A | | | GROUP B | | | GROUP C | |
| DAY 1 | | | | | | | | | |
| Ino (µM) | 0.6 | 7.2 | 18.3 | 3 | 27.5 | 20.3 | 3.1 | 1.2 | 0.4 |
| HX (µM) | 6.4 | 25.2 | 131.6 | 11.3 | 114.5 | 74.8 | 31.2 | 7.2 | 2.8 |
| X (µM) | 6.4 | 17.6 | 142.4 | 5.7 | 121.9 | 36.9 | 12.9 | 3.7 | 3.1 |
| UA (µM) | 103.1 | 847 | 2133.7 | 281.5 | 1861.7 | 1975.5 | 831.2 | 216.5 | 168.8 |
| DAY 15 | | | | | | | | | |
| Ino (µM) | 0.9 | 0.9 | 1.3 | 2.4 | 13 | 1.4 | 10.5 | 13.4 | 9.4 |
| HX (µM) | 78.6 | 86.5 | 206.8 | 11.2 | 47.7 | 72.9 | 690.3 | 1331.5 | 2256.7 |
| X (µM) | 320.7 | 541.5 | 556 | 11.7 | 61.9 | 33.7 | 493.1 | 2023.3 | 1190.4 |
| UA (µM) | 210.5 | 726.9 | 728.7 | 1021.2 | 1544.6 | 511.3 | 293.4 | 1239.1 | 1045.6 |

| SUBJECT ID | 11 | 12 | 13 | 14 | 15 | 16 |
|---|---|---|---|---|---|---|
| | | GROUP D | | | GROUP E | |
| DAY 1 | | | | | | |
| Ino (µM) | 24.9 | 2.4 | 4.2 | 0.8 | 29.2 | 7.5 |
| HX (µM) | 62.7 | 50 | 7.1 | 3.2 | 47.4 | 117.2 |
| X (µM) | 33 | 25.9 | 4.2 | 6.7 | 50.3 | 80.6 |
| UA (µM) | 1617 | 1526.3 | 518 | 282.3 | 2639 | 2198.5 |
| DAY 15 | | | | | | |
| Ino (µM) | 29.1 | 3.1 | 17.4 | 0.6 | 0.8 | 6 |
| HX (µM) | 1965.1 | 131.8 | 949.9 | 11.2 | 77.2 | 314 |
| X (µM) | 1474.8 | 22.7 | 1063.6 | 81.7 | 273.1 | 867.7 |
| UA (µM) | 649.2 | 1610.7 | 658.7 | 22.8 | 398.9 | 289.3 |

Fig.6

INTRACELLULAR ATP ENHANCER

TECHNICAL FIELD

The present invention relates to a human or animal intracellular ATP enhancer comprising a combination of A) a xanthine oxidase/xanthine dehydrogenase inhibitor and B) hypoxanthine, or a compound capable of being converted to hypoxanthine in the body. More specifically, the present invention relates to the intracellular ATP enhancer wherein A) is allopurinol or topiroxostat.

BACKGROUND ART

ATP (adenosine triphosphate, hereinafter sometimes simply referred to as ATP) is the most important compound that stores energy of living organism and supplies the energy when necessary, and it is considered that ATP reduction is related to pathological conditions of various diseases. For example, with regard to the causes of various types of hereditary hemolytic anemia, ATP reduction in erythrocytes is considered as a mechanism of hemolysis. Examples include sickle cell disease (Non-Patent Document 1), pyruvate kinase deficiency (Non-Patent Document 2), spherocytosis (Non-Patent Document 3), elliptocytosis (Non-Patent Document 3), stomatocytosis (Non-Patent Document 4), and thalassemia (Non-Patent Document 5), etc.

Additionally, intracellular ATP reduction is suggested as a mechanism of myocardial damage due to ischemic heart disease (Non-Patent Document 6), and it is reported that symptoms of chronic stable angina were suppressed by high-dose administration of a xanthine oxidase/xanthine dehydrogenase inhibitor, allopurinol (Non-Patent Document 7). The authors suggested that an increase in ATP due to allopurinol had a favorable effect on ischemic heart disease (Non-Patent Document 7).

Figure 6:
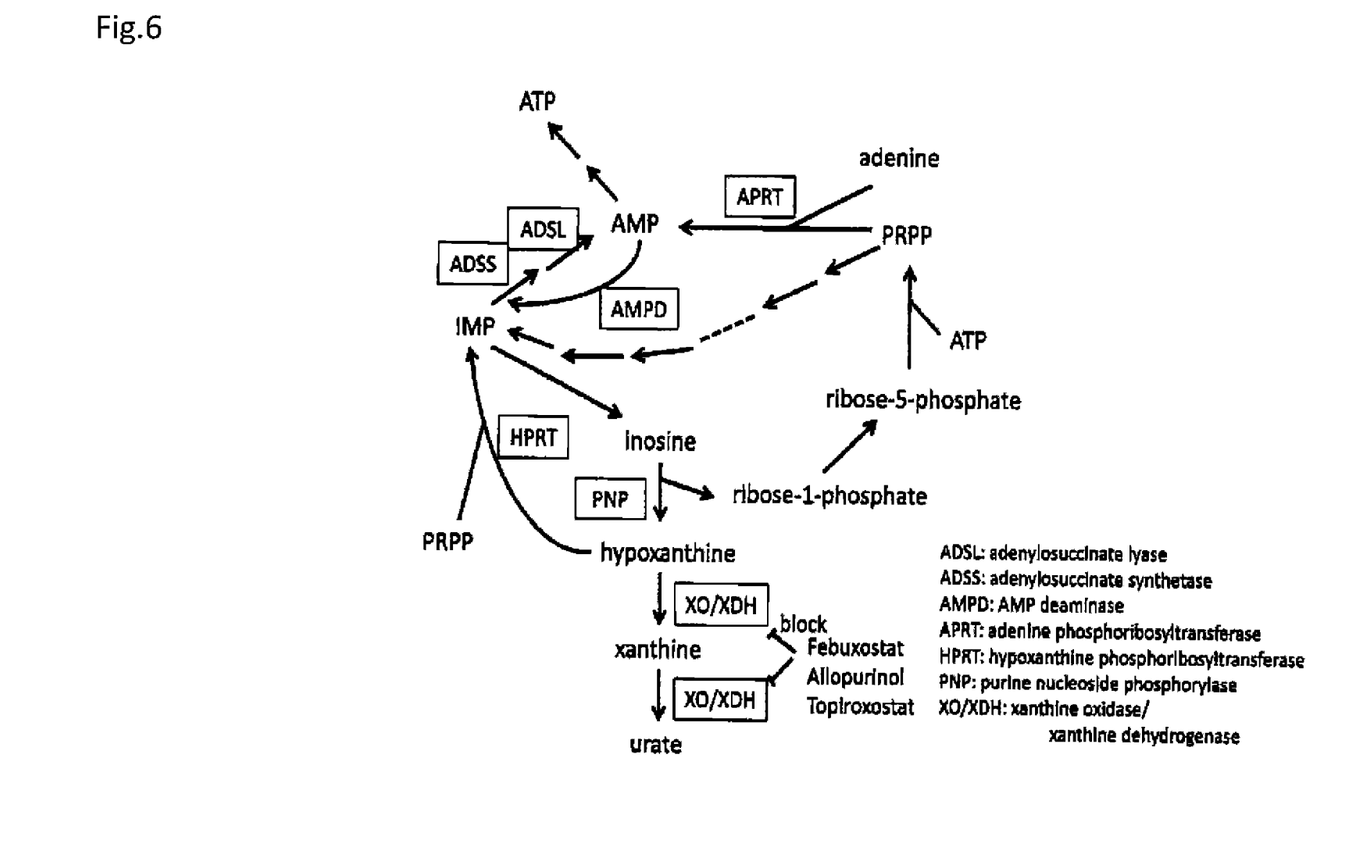
FIG. 6 is a diagram showing pathways involved in ATP synthesis.

Furthermore, an ATP enhancement therapy is likely to be effective for heart failure. Heart failure patients often undergo heart transplantation in the US and, instead of the period from occurrence of heart failure to death, a period from occurrence of heart failure to heart transplantation is used as a measure of the speed of progress of heart failure. A short period until heart transplantation indicates that the progress of heart failure is fast. In Europe and the US, the frequency of hereditary muscle AMP deaminase (AMPD) deficiency is extremely high, and about 20% of the general population has heterozygous deficiency. It is known from studies that people with muscle genetic AMPD deficiency have a longer period from heart failure to heart transplantation (Non-Patent Document 8). It is also suggested that an AMPD inhibitor improves heart failure in mice (Non-Patent Document 9). Generally, ATP of muscle decreases due to exercise. However, it is reported that people with hereditary muscle AMPD deficiency have intramuscular ATP not decreasing, or restrained from decreasing, after exercise (Non-Patent Document 10). Specifically, since AMP is not converted into IMP (inosine monophosphate, hereinafter sometimes simply referred to as IMP), AMP reduction can be prevented, and ATP reduction does not occur (FIG. 6). From above, it is considered that genetic muscle AMPD deficiency was less likely to cause ATP reduction in cardiomyocytes and suppressed the progress of heart failure.

It can be expected that enhancing ATP in this way improves pathological conditions of diseases in which a disease in ATP relates to the pathological conditions.

Although it is reported that inosine enhances muscular movement in expectation of occurrence of an enhancing action on muscular movement due to ATP increased by administration of inosine, a report denying the effect thereof is also made recently (Non-Patent Document 11).

However, it is possible that a cause of inability to prove inosine's muscular enhancing action is because inosine alone is not sufficient for completing the ATP enhancing action.

Nishino et al. have found that a xanthine oxidase/xanthine dehydrogenase inhibitor such as febuxostat administered to a model mouse of amyotrophic lateral sclerosis (hereinafter sometimes simply referred to as ALS) inhibits disease progression (Non-Patent Document 12). Nishino et al. speculate that an increase in ATP of nerve cells due to administration of febuxostat suppresses disease progression (Non-Patent Document 12). In fact, it is reported that knock-down of Na/K-ATPase in ALS model mice suppressed degeneration of nerve cells (Non-Patent Document 12). It is also reported that Na/K-ATPase activity is increased in ALS patients (Non-Patent Document 13). Therefore, it is considered that activation of Na/K-ATPase that reduces ATP promotes the onset or progression of ALS and that suppression of Na/K-ATPase that suppresses ATP reduction suppresses the progress of ALS.

Furthermore, it is reported that administration of inosine alleviates symptoms of Parkinson's disease (Non-Patent Document 14) and multiple sclerosis (Non-Patent Document 15). The authors of both documents believe that a decrease in serum uric acid value may be related to the diseases. Clinical trials are conducted for the purpose of raising the serum uric acid value by administering inosine, and producing a therapeutic effect. However, the effect is not enough in the past reports.

CITATION LIST

Non Patent Literature

Non-Patent Document 1: Palek J, Liu S C, Liu P A. Crosslinking of the nearest membrane protein neighbors in ATP depleted, calcium enriched and irreversibly sickled red cells. Prog Clin Biol Res. 1978; 20: 75-91.

Non-Patent Document 2: Glader B E. Salicylate-induced injury of pyruvate-kinase-deficient erythrocytes. N Engl J Med. 1976 Apr. 22; 294(17): 916-8.

Non-Patent Document 3: de Jong K, Larkin S K, Eber S, Franck P F, Roelofsen B, Kuypers F A. Hereditary spherocytosis and elliptocytosis erythrocytes show a normal transbilayer phospholipid distribution. Blood. 1999 Jul. 1; 94(1): 319-25.

Non-Patent Document 4: Mentzer W C Jr, Smith W B, Goldstone J, Shohet S B. Hereditary stomatocytosis: membrane and metabolism studies. Blood. 1975 November; 46(5): 659-69.

Non-Patent Document 5: Wiley JS. Increased erythrocyte cation permeability in thalassemia and conditions of marrow stress. J Clin Invest. 1981 April; 67(4): 917-22.

Non-Patent Document 6: Vogt A M, Ackermann C, Yildiz M, Schoels W, Kubler W. Lactate accumulation rather than ATP depletion predicts ischemic myocardial necrosis: implications for the development of lethal myocardial injury. Biochim Biophys Acta. 2002 Mar. 16; 1586(2): 219-26

Non-Patent Document 7: Noman A, Ang D S, Ogston S, Lang C C, Struthers A D. Effect of high-dose allopurinol on exercise in patients with chronic stable angina: a randomised, placebo controlled crossover trial. Lancet. 2010 Jun. 19; 375(9732): 2161-7.

Non-Patent Document 8: Loh E, Rebbeck T R, Mahoney P D, DeNofrio D, Swain J L, Holmes E W. Common variant in AMPD1 gene predicts improved clinical outcome in patients with heart failure. Circulation. 1999 Mar. 23; 99(11): 1422-5.

Non-Patent Document 9: Borkowski T, Slominska E M, Orlewska C, Chlopicki S, Siondalski P, Yacoub M H, Smolenski R T. Protection of mouse heart against hypoxic damage by AMP deaminase inhibition. Nucleosides Nucleotides Nucleic Acids. 2010 June; 29(4-6): 449-52.

Non-Patent Document 10: Norman B, Sabina R L, Jansson E. Regulation of skeletal muscle ATP catabolism by AMPD1 genotype during sprint exercise in asymptomatic subjects. J Appl Physiol (1985). 2001 July; 91(1): 258-64.

Non-Patent Document 11: McNaughton L, Dalton B, Tarr J. Inosine supplementation has no effect on aerobic or anaerobic cycling performance. Int J Sport Nutr. 1999 December; 9(4): 333-44.

Non-Patent Document 12: Yasuko Abe, Shinsuke Kato, Takeshi Nishino. Therapeutic agent for amyotrophic lateral sclerosis. U.S. Pat. No. 8,318,792 B2, European Patent EP 2050467 A1

Non-Patent Document 13: Gallardo G, Barowski J, Ravits J, Siddique T, Lingrel J B, Robertson J, Steen H, Bonni A. An α2-Na/K ATPase/α-adducin complex in astrocytes triggers non-cell autonomous neurodegeneration. Nat Neurosci. 2014 December; 17(12): 1710-9.

Non-Patent Document 14: Parkinson Study Group SURE-PD Investigators, Schwarzschild M A, Ascherio A, Beal M F, Cudkowicz M E, Curhan G C, Hare J M, Hooper D C, Kieburtz K D, Macklin E A, Oakes D, Rudolph A, Shoulson I, Tennis M K, Espay A J, Gartner M, Hung A, Bwala G, Lenehan R, Encarnacion E, Ainslie M, Castillo R, Togasaki D, Barles G, Friedman J H, Niles L, Carter J H, Murray M, Goetz C G, Jaglin J, Ahmed A, Russell D S, Cotto C, Goudreau J L, Russell D, Parashos S A, EdeP, Saint-Hilaire M H, Thomas C A, James R, Stacy M A, Johnson J, Gauger L, Antonelle de Marcaida J, Thurlow S, Isaacson S H, Carvajal L, Rao J, Cook M, Hope-Porche C, McClurg L, Grasso D L, Logan R, Orme C, Ross T, Brocht A F, ConstantinescuR, Sharma S, Venuto C, Weber J, Eaton K. Inosine to increase serum and cerebrospinal fluid urate in Parkinson disease: a randomized clinical trial. JAMA Neurol. 2014 February; 71(2): 141-50.

Non-Patent Document 15: Markowitz C E, Spitsin S, Zimmerman V, Jacobs D, Udupa J K, Hooper D C, Koprowski H. The treatment of multiple sclerosis with inosine. J Altern Complement Med. 2009 June; 15(6): 619-25.

Non-Patent Document 16: Ogasawara N, Goto H, Yamada Y, Nishigaki I, Itoh T, Hasegawa I, Park K S. Deficiency of AMP deaminase in erythrocytes. Hum Genet. 1987 January; 75(1): 15-8.

SUMMARY OF INVENTION

Technical Problem

It is reported that intracellular ATP can be increased to some extent even by administration of inosine alone. In fact, in a report by Ogasawara et al., erythrocytes were left to stand at low temperature for 20 to 30 days to prepare erythrocytes with low ATP, and inosine was added thereto, followed by leaving the erythrocytes to stand for 1 hour. As a result, ATP increased (Non-Patent Document 16). However, inosine is rapidly metabolized in human bodies through hypoxanthine and xanthine to uric acid (FIG. 6). Therefore, use of inosine alone was not enough to produce a sufficient ATP enhancing action. Moreover, although administration of febuxostat alone can be expected to enhance intracellular ATP to some extent, this alone may be insufficient.

A problem to be solved by the present invention is to provide a composition having an effect of enhancing intracellular ATP, and, in particular, an ATP enhancer surpassing the enhancing effect of inosine or febuxostat alone.

Solution to Problem

To solve the problems described above, the present invention has the following configurations.

(1) A human or animal intracellular ATP enhancer comprising a combination of the following A) and B):
A) a xanthine oxidase/xanthine dehydrogenase inhibitor; and
B) hypoxanthine, or a compound capable of being converted to hypoxanthine in the body.
(2) The intracellular ATP enhancer according to (1), wherein A) is any one or more selected from febuxostat, topiroxostat, allopurinol, hydroxyalkane, carprofen, Y-700, and KUX-1151.
(3) The intracellular ATP enhancer according to (1) or (2), wherein B) the compound capable of being converted to hypoxanthine in the body is any one or more compounds selected from inosine, inosinic acid, adenine, adenosine, AMP, ADP, ATP, succinyladenosine, S-adenosylmethionine, S-adenosylhomocysteine, methylthioadenosine, and pharmaceutically acceptable salts thereof.
(4) The ATP enhancer according to any one of (1) to (3), wherein the combination of A) and B) is a combination drug or a kit formulation containing A) and B).
(5) Allopurinol or topiroxostat used in combination with inosine as an intracellular ATP enhancer.

Advantageous Effects of Invention

The ATP enhancing effect of the combined administration of A) and B) of the present invention enables provision of a drug for treating various diseases in which the reduction of ATP forms a portion of pathological conditions, furthermore various diseases in which progression of the pathological conditions is suppressed by excessive supply of ATP:
A) A xanthine oxidase/xanthine dehydrogenase inhibitor
B) Hypoxanthine, or a compound capable of being converted to hypoxanthine in the body.

DESCRIPTION OF EMBODIMENTS

One active ingredient of the present invention is A) a xanthine oxidase/xanthine dehydrogenase inhibitor. Examples of the xanthine oxidase/xanthine dehydrogenase inhibitor include febuxostat (trade name, Feburic (Teijin Pharma Limited)), topiroxostat (trade name, Uriadec (Sanwa Kagaku Kenkyusho Co., Ltd.), Topiloric (Fujiyakuhin Co., Ltd.)), allopurinol (trade name, Zyloric (GlaxoSmithKline K.K.)), hydroxyalkane, carprofen, Y-700 (Mitsubishi Tanabe Pharma), and KUX-1151 (Kissei Pharmaceutical Co., Ltd.). Examples of the active component A) in the present invention also include pharmaceutically acceptable salts thereof.

Another active ingredient of the present invention is B) hypoxanthine, or a compound capable of being converted to hypoxanthine in the body. Examples of the compound capable of being converted to hypoxanthine in the body include any one or more compounds selected from inosine, inosinic acid, adenine, adenosine, AMP, ADP, ATP, succinyladenosine, S-adenosylmethionine, S-adenosylhomocysteine, methylthioadenosine, and pharmaceutically acceptable salts thereof. Since these compounds are eventually degraded into hypoxanthine, these substances may be used instead of inosine (FIG. 6). Among them, inosine is desirable.

The intracellular ATP enhancing action of the present invention refers to an effect that the active ingredients of the present invention increase generation of ATP in the cells. The increase is used to mean either an increasing, or suppressing of decrease, from a steady state, or bringing a reduced state closer to the steady state. The effect of the present invention can be confirmed by directly measuring the intracellular ATP concentration as well as by indirectly measuring a product of another metabolic pathway induced by an increase in ATP.

"Comprising a combination of A) and B)" of the present invention is used to mean all the forms in which the components A) and B) are combined such that the components are administered to exert an ATP enhancing action in the body of a subject of administration. Therefore, this includes either a combination drug (also referred to as compounding drugs) of the components A) and B) mixed to form a composition, or drugs presented together to be administered in the same period at the time of administration although physically present separately without being mixed.

Examples of the combination drug (compounding drug) include those mixed as a drug formulation. Examples of the drug formulation include oral agents such as granules, powders, solids formulations, liquids and inhalants.

Examples of the drugs presented together to be administered in the same period at the time of administration although physically present separately include so-called kit formulation and a form of being packed in one bag.

The same period does not necessarily mean the same time in a strict sense, and the same period of the present invention includes the case that an interval exists within a range in which the ATP enhancing effect of the present invention is exerted. For example, when one is taken before meal and the other is taken after meal, this corresponds to the case of administering in the same period of the present invention.

The present invention can also be understood as a method of enhancing intracellular ATP or a method of increasing ATP, comprising a step of combined administration of A) and B).

The dosage of the ATP enhancer of the present invention is desirably, for example, about 50 to 800 mg/day for allopurinol of A), 40 to 160 mg/day for topiroxostat, and 10 to 80 mg/day for febuxostat. In addition, the dosage is desirably 0.5 to 4.0 g/day for inosine of B), and for the case of B) being hypoxanthine or a compound capable of being converted to hypoxanthine in the body, the effective dosage can be determined by calculation of the amount that corresponds to an amount of inosine based on the molecular weights.

With regard to an administration method, each of the dosages can be administered once a day, or divided twice or more a day. Among them, febuxostat is desirably administered twice a day rather than once a day as in conventional usage of febuxostat. It is also desirable that inosine is administered twice a day rather than once a day. Therefore, both inosine and febuxostat are more desirably divided and administered twice a day. It is also desirable that allopurinol or topiroxostat is administered twice a day rather than once a day.

In cases of a combination drug, adjustment may be made in consideration of a daily dosage and an administration method. For example, the combination drug is desirably adjusted by adding 0.5 g, 1 g, 1.5 g, or 2 g of inosine to 100 mg of allopurinol, 80 mg of topiroxostat, or 20 mg or 40 mg of febuxostat.

The dosage form of the pharmaceutical of the present invention is not limited, and may be either oral administration or parenteral administration. The pharmaceutical may be made into an appropriate formulation depending on the dosage form. For example, the pharmaceutical may be prepared into various formulations such as injection solutions, oral preparations including capsules, tablets, granules, powders, balls, and fine granules; rectally administered drugs; oleaginous suppositories and aqueous suppositories.

Since the pharmaceutical of the present invention contains the active components A) and B), the dosage form of the active component A) may be either the same as or different from the dosage form of the active component B). Examples of the cases of the same dosage form include cases where both components are orally administered as tablets, cases where the components are orally administered as a combination drug containing both, and cases where the components are administered as an injection solution in which both are mixed. Examples of the cases of different dosage forms include cases where one component is administered as an oral formulation while the other is administered as an injection solution or the like.

The subject of administration of the present invention is a human or an animal and is a human or an animal in a condition requiring enhancement of ATP.

Target disease include the following diseases in which a relation of ATP reduction to pathological conditions is strongly suggested, i.e., (1) hemolytic anemia, (2) ischemic heart disease, (3) heart failure, (4) amyotrophic lateral sclerosis, (5) Parkinson's disease, and (6) ADSL deficiency. Among them, the present invention is particularly effective for (2) ischemic heart disease, (3) heart failure, and (4) amyotrophic lateral sclerosis.

The ATP enhancer of the present invention can further be combined with other medicines within the range not to impair the action of the present invention.

The present invention will now specifically be described based on examples; however, the present invention is not limited thereto.

EXAMPLES

[Test Example 1] Clinical Trial (Combined Administration of Febuxostat and Inosine)

1. Measurement Methods (1) Clinical Examination

Measurement was performed by conventional methods except for the following items.

(2) Serum Uric Acid Value

For a clinical chemistry automatic analyzer, a dry clinical chemistry analysis measuring unit manufactured by ARKRAY, Inc. was used, and the serum uric acid value was measured by using the uricase-peroxidase method.

(3) Urinary Uric Acid Concentration/Creatinine Concentration

Since the urinary uric acid concentration varies with urine volume, a urinary uric acid amount was evaluated by using a urinary uric acid/creatinine value acquired by dividing by urinary creatinine concentration. The measurement method of the uric acid value was the same as that for the serum uric acid value.

(4) Blood Purine Concentrations

Various purines in peripheral blood were measured according to the Reference. Briefly, peripheral blood was collected with EDTA, 500 µL mixed with 500 µL ice cold 8% PCA, immediately vortexed for five seconds, and centrifuged at 12,000×g for 10 minutes at 4° C., and the supernatant was stored at −80° C. The processed sample was then dissolved, with 40 µL of 2M $K_2CO_3$ in 6 M KOH added to 650 µL of the solution to simultaneously precipitate the PCA and neutralize the solution. After this solution was centrifuged at 12,000×g for 10 minutes at 4° C., 160 µL of a mobile phase was added to 40 µL of the supernatant and applied to HPLC. The conditions of HPLC were also set according to the Reference. The amounts of purines are expressed in molar quantity contained in 1 L of whole blood.

REFERENCE

Coolen E J, Arts I C, Swennen E L, Bast A, Stuart M A, Dagnelie P C. Simultaneous determination of adenosine triphosphate and its metabolites in human whole blood by RP-HPLC and UV-detection. J Chromatogr B Analyt Technol Biomed Life Sci. 2008 Mar. 15; 864(1-2): 43-51.

(5) Urinary Purine Concentrations

The purine concentrations were measured by the same method as in (4).

2. Administration Test (1) Test Subjects

The following administration test was conducted for 16 Japanese healthy adult males, one subject in Phase I and 15 subjects in Phase II divided into Group A to Group E with 3 subjects each.

(2) Administration Details and Administration Schedule (2-1) Phase I

Safety was confirmed by simultaneous administration of 20 mg of febuxostat and 500 mg of inosine twice a day for 14 days to one subject.

(2) Phase II

After Phase I, the following contents were administered to three subjects in each group:
  Group A: febuxostat 20 mg twice a day for 14 days;
  Group B: inosine 500 mg of twice a day for 14 days;
  Group C: febuxostat 20 mg and inosine 500 mg twice a day for 14 days;
  Group D: febuxostat 20 mg and inosine 1000 mg twice a day for 14 days; and
  Group E: febuxostat 30 mg twice a day for 14 days.

3. Results 3-1. Phase I (1) Adverse Events (1-1) Physical Findings Etc.

The subject had no adverse events in terms of subjective findings and physical findings.

(1-2) Clinical Examination

AST showed an abnormal value of 49 U/L (reference value: 10 to 40) on Day 8 and returned to a reference value of 29 U/L on Day 15. The creatinine showed an abnormal value of 1.09 mg/dL (reference value: 0.61 to 1.04) on Day 8 and returned to a reference value of 0.98 mg/dL on Day 15. The blood glucose level showed abnormal values of 66 mg/dL on Day 8 and 67 mg/dL on Day 15 (reference value: 70 to 109).

(2) Changes in Serum Uric Acid Value

The serum uric acid value was 4.9 mg/dL on Day 1, 2.5 mg/dL on Day 8, and 2.9 mg/dL on Day 15. Taking 40 mg of febuxostat and 1 g of inosine resulted in a reduction of 2.2 mg/dL on average.

3-2. Phase II (1) Adverse Events (1-1) Physical Findings

No significant difference existed between groups in terms of age, height, weight, BMI, systolic blood pressure, diastolic blood pressure, pulse rate, and body temperature. No significant change was seen in the systolic blood pressure, diastolic blood pressure, pulse rate, and body temperature, except a significant increase in the pulse rate observed in one subject.

(1-2) Adverse Events of Test Values (Excluding Uric Acid Value)

Measurement was performed on total protein, albumin, total bilirubin, AST, ALT, AL-P, LD, γ-GT, total cholesterol, neutral fat, HDL cholesterol, LDL cholesterol determinate quantity, uric acid, urea nitrogen, creatinine, sodium, chloride, potassium, calcium, blood glucose test, HbA1c (NGSP), white blood cell count WBC, red blood cell count RBC, hemoglobin level Hb, hematocrit Ht, platelet count PLT, BASO, EOSINO, NEUTRO, LYMPH, and MONO.

No particular difference was observed in the background of the groups. No particular significant change was recognized except the serum uric acid value.

(2) Changes in Serum Uric Acid Value

Figure 1:
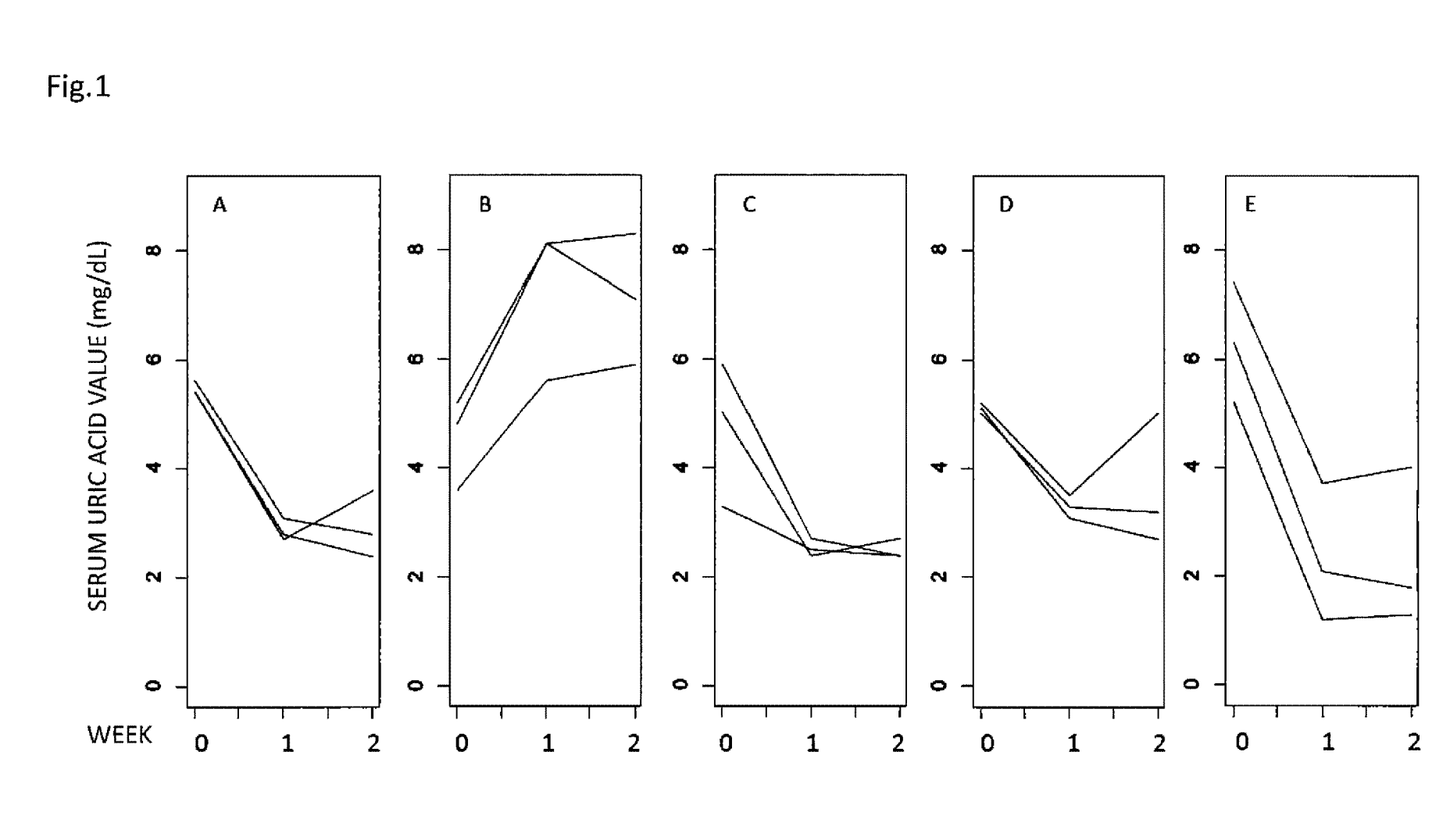
FIG. 1 is graphs showing changes in the serum uric acid value with time in the case of administration to Groups A to E. The horizontal axis indicates the measurement period (weeks), and the vertical axis indicates the serum uric acid value (unit, mg/dL). Group A: febuxostat 20 mg twice a day for 14 days; Group B: inosine 500 mg twice a day for 14 days; Group C: febuxostat 20 mg+inosine 500 mg twice a day for 14 days; Group D: febuxostat 20 mg+inosine 1000 mg twice a day for 14 days; Group E: febuxostat 30 mg twice a day for 14 days (the same applies to the following figures).

FIG. 1 shows graphs of respective Groups A to E. A significant increase in serum uric acid value was observed in Group B to which only inosine was administered (up to 8.1 mg/dL). In Groups A and C to E, a decrease in serum uric acid value was observed. The serum uric acid value was not reduced to less than 2 mg/dL in any of the administration examples of 40 mg/day of febuxostat; however, the serum uric acid value less than 2 mg/dL was observed in the example of Group E to which 60 mg/day of febuxostat was administered.

The serum uric acid value was reduced by 2.53 mg/dL due to the administration of 40 mg/dL of febuxostat (Group A), and was reduced by 2.23 mg/dL (Group C) and 1.47 mg/dL (Group D) in the examples of administering 1 g or 2 g per day of inosine, respectively, at the same time of febuxostat administration.

The serum uric acid value was reduced by 3.93 mg/dL due to administration of 60 mg/dL of febuxostat (Group E). The serum uric acid value was raised by 2.57 mg/dL on average due to 1 g per day of inosine (Group B). Examining this result in terms of the serum uric acid value increasing effect of inosine in the presence of administration of febuxostat, the serum uric acid value increased by 0.3 mg/dL due to 1 g/day administration of inosine, and was increased by 1.06 mg/dL due to 2 g/day administration of inosine, in the presence of 40 mg/day of febuxostat. As described above, the serum uric acid value was increased by 2.57 mg/dL due to 1 g/day administration of inosine without administration of febuxostat, and therefore, the serum uric acid raising action of inosine is considerably suppressed in the presence of administration of febuxostat.

(3) Urinary Uric Acid Concentration/Creatinine Concentration

Figure 2:
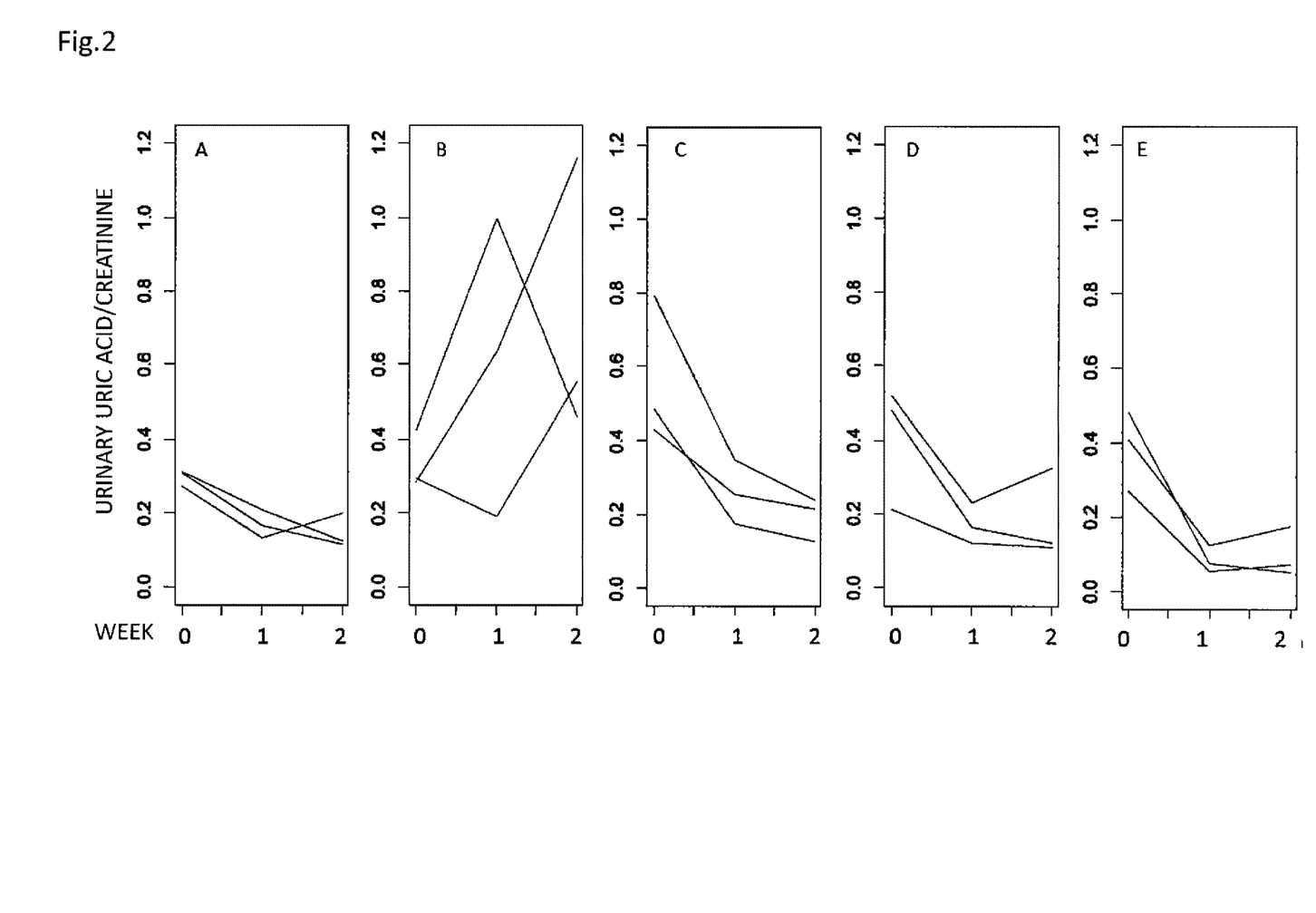
FIG. 2 is graphs showing changes in the urinary uric acid concentration/creatinine concentration with time in the case of administration to Groups A to E. The horizontal axis indicates the measurement period (weeks), and the vertical axis indicates the urinary uric acid concentration/creatinine concentration (ratio).

Changes in urinary uric acid concentration/creatinine concentration of the respective groups from Week 0 to Week 2 are shown in FIG. 2. The urinary uric acid/creatinine was significantly increased only in Group B due to administration of inosine. The urinary uric acid/creatinine was reduced in all of Groups A and C to G. These changes in the urinary uric acid concentration/creatinine concentration were almost the same as the change pattern of the serum uric acid value.

(4) Blood Purine Concentration

Figure 3:
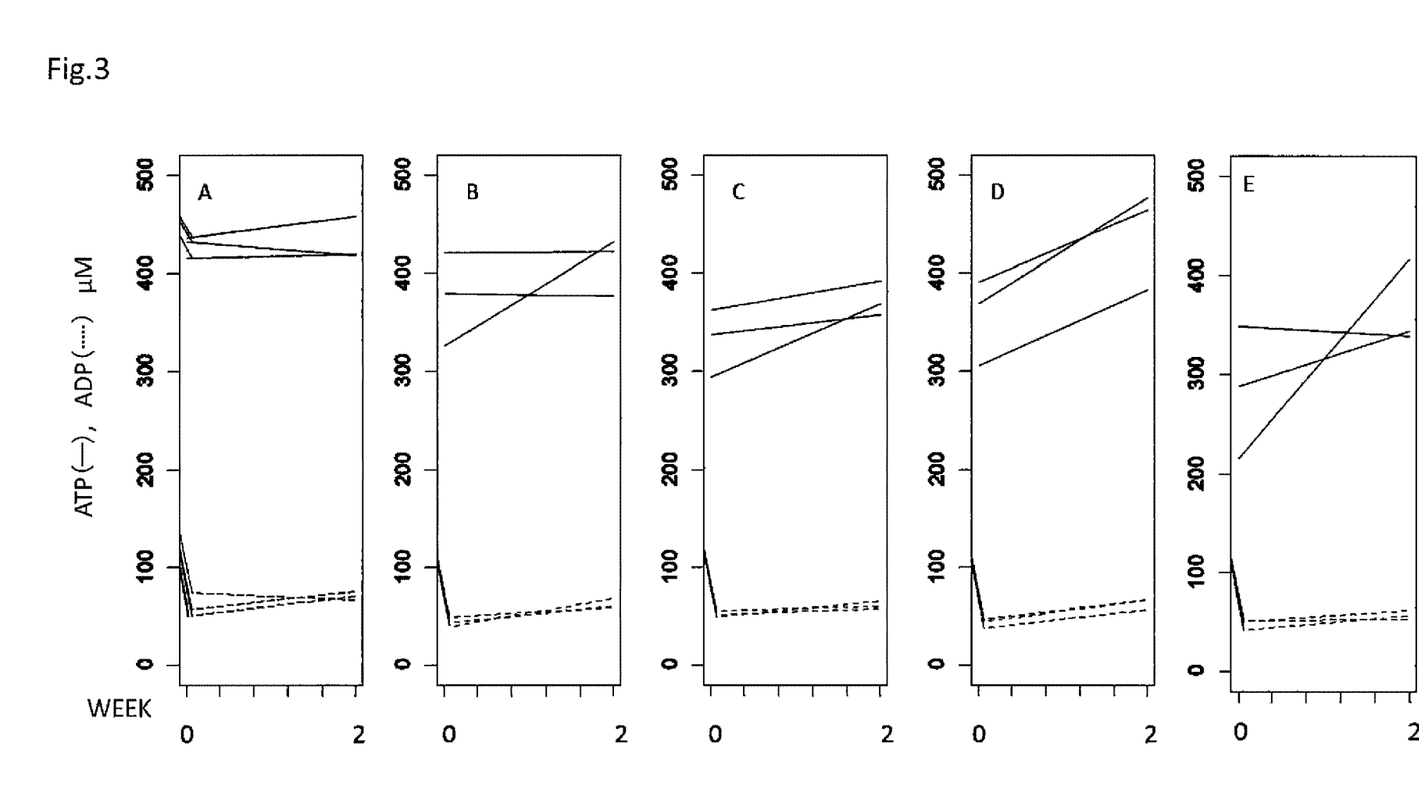
FIG. 3 is graphs showing changes in blood ATP and ADP with time in the case of administration to Groups A to E. The horizontal axis indicates the measurement period (weeks), and the vertical axis indicates the ATP or ADP concentration (unit, µM). ATP: solid line; ADP: broken line.
Figure 4:
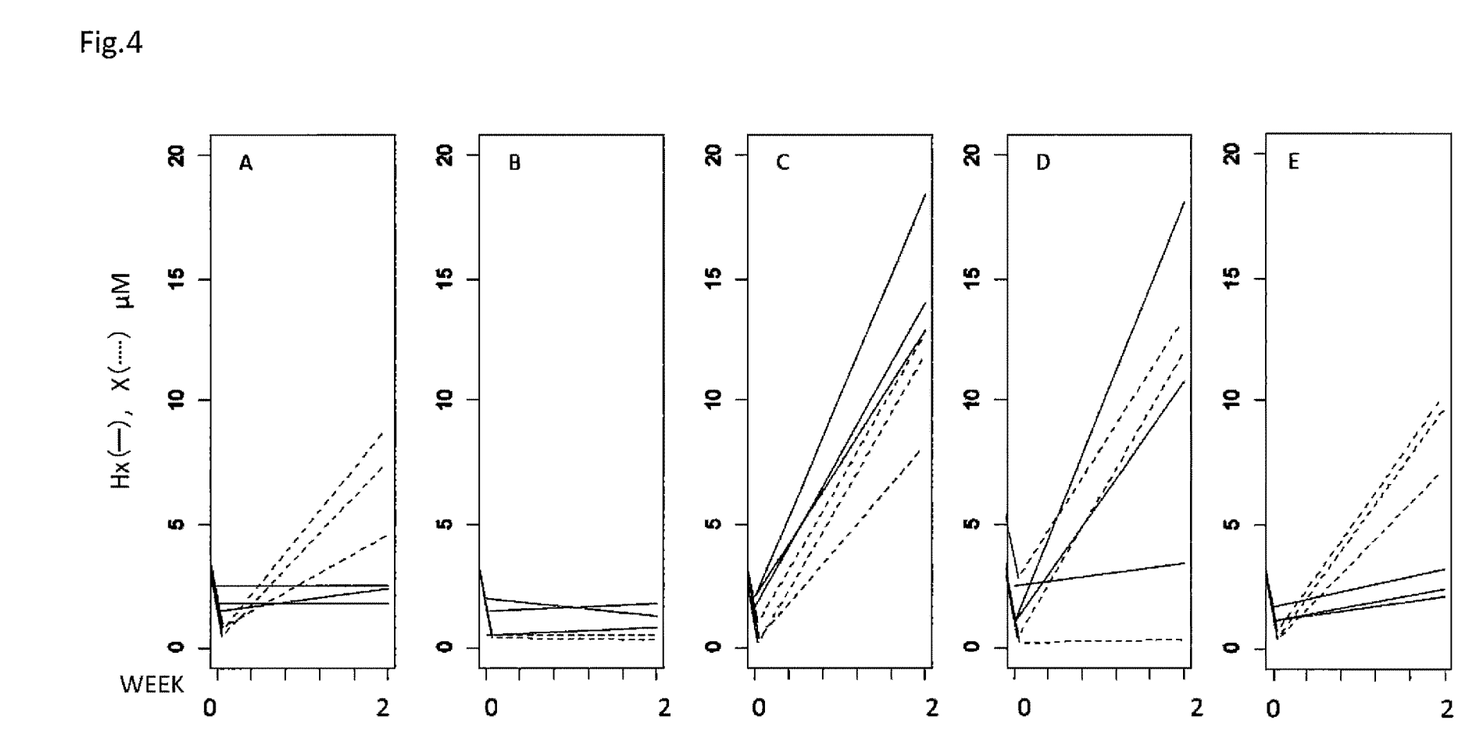
FIG. 4 is graphs showing changes in blood Hx (hypoxanthine) and X (xanthine) with time in the case of administration to Groups A to E. The horizontal axis indicates the measurement period (weeks), and the vertical axis indicates the Hx or X concentration (unit, µM). Hx: solid line; X: broken line.

Changes in the concentrations of purines in blood of the respective groups from Week 0 to Week 2 are shown in FIGS. 3 and 4.

FIG. 3 shows the concentration of blood ATP/ADP in Groups A to E. The ATP concentration was not changed in Groups A and B, and a rise in ATP was suggested in Groups C and D. No certain tendency was observed in Group E. Therefore, although no rise in ATP was observed due to single administration of febuxostat or inosine, a rise in ATP was observed in the combined use examples, especially in the examples of 40 mg/day of febuxostat and 1 to 2 g/day of inosine. No certain tendency was observed from the combined use of febuxostat and inosine exceeding these amounts.

FIG. 4 shows the concentrations of hypoxanthine (Hx) and xanthine (X) in blood for each of Groups A to E. In the group of administration of 40 mg/day of febuxostat alone (Group A), the Hx concentration was unchanged, while X was significantly increased. In the group of administration of 1 g/day of inosine alone (Group B), neither Hx nor X changed. Although the inosine concentration in blood was also measured, no rise in the concentration of inosine was observed in any groups including the groups of single administration of inosine (Groups A to E). From these results, it is considered that the concentration of the enzyme converting inosine to Hx, i.e., purine nucleoside phosphorylase (PNP), is extremely high in blood, resulting in a rapid decomposition of inosine to Hx and further decomposition of Hx to X. In the examples of using 40 mg/day of febuxostat in combination with 1 to 2 g/day of inosine, a significant rise was recognized in both Hx and X. Therefore, the effect of "rise in Hx in blood" not observed with febuxostat alone or inosine was observed due to the combined use (FIG. 4).

In the single administration example of 60 mg/day of febuxostat, a slight rise in Hx was observed along with a rise in X (FIG. 4E).

(5) Urinary Purine Concentrations

Figure 5:
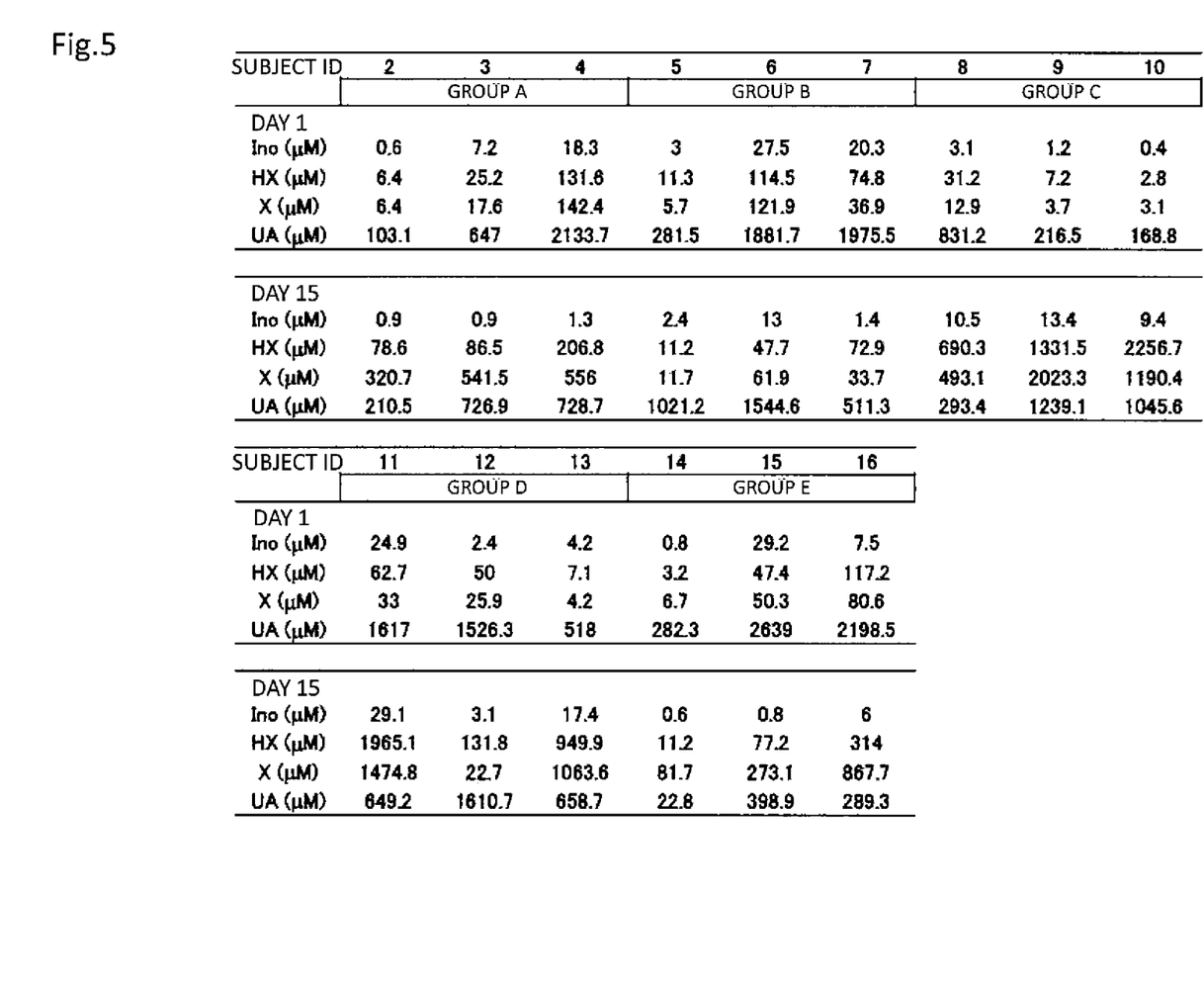
FIG. 5 is a table showing changes in the concentrations (µM) of various urinary purines with time in the case of administration to Groups A to E.

Changes in concentrations of urinary inosine, Hx, X, and uric acid of the respective groups from Week 0 to Week 2 are shown in FIG. 5. The urinary Hx showed a moderate rise in the single administration example of febuxostat and showed a significant rise in the combined use example of febuxostat and inosine. In the single administration example of inosine, no rise in Hx or X was recognized. Although the concentration of X significantly increased also in the single administration example of febuxostat, the concentration was further significantly increased in the combined use example of febuxostat and inosine.

The maximum concentrations of urinary X in the respective groups were 556.0 µM in Group A, 61.9 µM in Group B, 2023.3 µM in Group C, 1474.8 µM in Group D, and 867.7 µM in Group E. Therefore, in the examples of using 40 mg of febuxostat in combination with 1 and 2 g of inosine, the maximum urinary X concentration were 3.64 and 2.65 times larger as compared to the single administration group of 40 mg of febuxostat.

4. Discussion on Test Example 1

(1) The combined use of febuxostat and inosine was safe at a dosage equal to or less than 40 mg/day of febuxostat and 2 g/day of inosine in the two-week continuous dosing test. Although an increase in ATP in blood was observed in these combined use groups, such a change was not observed in the other single administration groups.

(2) A significant decrease in the serum uric acid value was observed in the single administration of febuxostat, a significant increase in the serum uric acid value was observed in the single administration of inosine, and a moderate reduction was observed in the combined therapy.

(3) No increase in inosine was observed in any group and it was considered that inosine was metabolized to Hx by PNP.

(4) In the single administered group of inosine, Hx or X did not increase in blood or urine, and it was considered that Hx and X were changed to uric acid.

(5) In the single administration group of febuxostat, X moderately increased and Hx increased to a slight to moderate degree in both blood and urine.

(6) In the combined use of febuxostat and inosine, Hx and X significantly increased in both blood and urine. It is considered that an increase in Hx in blood causes an increase in ATP.

(7) From the clinical test described above, a pharmacological action, which was impossible for single administration of inosine and febuxostat, was recognized from the combined use thereof. The present invention enables the enhancement of hypoxanthine and ATP in blood, which is a novel pharmacological action that has not existed before.

[Test Example 2] Clinical Trial (2)

The Test Example 1 showed an ATP enhancing action by combined use of febuxostat and inosine, to an extent to which such an action cannot be observed when febuxostat or inosine was administered alone. In view of this, tests were carried out to investigate whether similar action effects can be produced with allopurinol or topiroxostat, which are xanthine oxidase/xanthine dehydrogenase inhibitors similar to febuxostat.

1. Administration Test
(1) Test Subjects

The following administration test was conducted for 15 Japanese healthy adult males, who were divided into Groups A, B, and C, with 5 subjects in each group.

(2) Administration Details and Administration Schedule

Group A: allopurinol 100 mg and inosine 500 mg twice a day for 14 days;
Group B: topiroxostat 80 mg and inosine 500 mg twice a day for 14 days;
Group C: febuxostat 20 mg and inosine 500 mg twice a day for 14 days.

2. Results
(1) Changes in Serum Uric Acid Value

The mean serum uric acid values before the test and after the test in Groups A to C are shown below in Table 1. In all groups, the serum uric acid value decreased after the administration of the ATP enhancer of the present invention.

TABLE 1

|  | Day 1 (Before the test) (mg/dL) | Day 15 (After completion of the test) (mg/dL) | Amount changed (mg/dL) |
| --- | --- | --- | --- |
| Group A | 5.58 | 4.54 | −1.04 |
| Group B | 5.78 | 3.46 | −2.32 |
| Group C | 6.10 | 2.30 | −3.80 |

(2) Hypoxanthine Concentration

The mean hypoxanthine concentrations before the test and after the test in Groups A to C are shown below in Table 2. In all groups, hypoxanthine in blood considerably increased after the administration of the ATP enhancer of the present invention.

TABLE 2

|  | Day 1 (Before the test) (μM) | Day 15 (After completion of the test) (μM) | Amount changed (μM) |
| --- | --- | --- | --- |
| Group A | 1.67 | 8.95 | 7.28 |
| Group B | 1.41 | 9.19 | 7.78 |
| Group C | 1.77 | 10.49 | 8.72 |

(3) ATP Concentration

The mean blood ATP concentrations before the test and after the test in Groups A to C are shown below in Table 3. In all groups, ATP in blood increased after the administration of the ATP enhancer of the present invention.

TABLE 3

|  | Day 1 (Before the test) (μM) | Day 15 (After completion of the test) (μM) | Amount changed (μM) |
| --- | --- | --- | --- |
| Group A | 334.2 | 358.6 | 24.4 |
| Group B | 334.5 | 342.9 | 8.4 |
| Group C | 338.3 | 354.5 | 16.2 |

3. Discussion

Increases in hypoxanthine and ATP in blood were observed after the combined use of febuxostat and inosine, the combined use of topiroxostat and inosine, or the combined use of allopurinol and inosine. It is considered that all of these cases were caused by increases in intracellular ATP due to suppression of xanthine oxidase/xanthine dehydrogenase by febuxostat, topiroxostat, or allopurinol which occurred at the same time as accumulation of hypoxanthine produced by degradation of inosine by purine nucleoside phosphorylase in the body. Such a phenomenon causing increases in hypoxanthine and ATP occurs only in cases where the supply from inosine and the suppression of xanthine oxidase/xanthine dehydrogenase occur at the same time.

This is because the increases in hypoxanthine and ATP did not occur when a xanthine oxidase/xanthine dehydrogenase inhibitor was administered alone, or when inosine was administered alone (Test Example 1). Therefore, in Test Example 1, neither an increase in hypoxanthine nor an increase in ATP occurred when febuxostat or inosine was administered alone (FIGS. 4A and 4B; FIGS. 3A and 3B), but their combined use caused increases in hypoxanthine and ATP (FIGS. 4C and 4D, FIGS. 3C and 3D).

Therefore, it suggested that the phenomenon causing increases in hypoxanthine and ATP occurs only in cases where a xanthine oxidase/xanthine dehydrogenase inhibitor and inosine were administered in combination.

[Formulation Example 1] Combination Drug Example

A combination drug (tablet type) for oral administration was manufactured, having the following contents per tablet.
Allopurinol: 100 mg
Inosine: 0.5 g
Alpha starch (disintegrating binder): 70 mg
Silicified microcrystalline cellulose (filler): 32.656 mg
Croscarmellose sodium (disintegrator): 10 mg
Magnesium stearate (lubricant): 0.8 mg

[Formulation Example 2] Kit Formulation Example

Tablets having the composition of A below containing allopurinol, and a medicine having the composition of B below containing inosine were manufactured and put in the same bag separated to prevent mixing with each other for adjustment into one dose, i.e., a daily dose, thereof in the same box.
A. Allopurinol Tablet
Allopurinol: 100 mg
Alpha starch (disintegrating binder): 70 mg
Silicified microcrystalline cellulose (filler): 32.656 mg
Croscarmellose sodium (disintegrator): 10 mg
Magnesium stearate (lubricant): 0.8 mg
B. Inosine
Inosine: 0.5 g

[Formulation Example 3] Combination Drug Example

A combination drug (tablet type) for oral administration was manufactured, having the following contents per tablet.
Topiroxostat: 80 mg
Inosine: 0.5 g
Alpha starch (disintegrating binder): 70 mg
Silicified microcrystalline cellulose (filler): 32.656 mg
Croscarmellose sodium (disintegrator): 10 mg
Magnesium stearate (lubricant): 0.8 mg

[Formulation Example 4] Kit Formulation Example

Tablets having the composition of A below containing topiroxostat, and a medicine having the composition of B below containing inosine were manufactured and put in the same bag separated to prevent mixing with each other for adjustment into one dose, i.e., a daily dose, thereof in the same box.

A. Topiroxostat tablet
  Topiroxostat: 80 mg
  Alpha starch (disintegrating binder): 70 mg
  Silicified microcrystalline cellulose (filler): 32.656 mg
  Croscarmellose sodium (disintegrator): 10 mg
  Magnesium stearate (lubricant): 0.8 mg
B. Inosine
  Inosine: 0.5 g

[Formulation Example 5] Combination Drug Example

A combination drug (tablet type) for oral administration was manufactured, having the following contents per tablet.
  Febuxostat: 20 mg
  Inosine: 0.5 g
  Alpha starch (disintegrating binder): 70 mg
  Silicified microcrystalline cellulose (filler): 32.656 mg
  Croscarmellose sodium (disintegrator): 10 mg
  Magnesium stearate (lubricant): 0.8 mg

[Formulation Example 6] Kit Formulation Example

Tablets having the composition of A below containing febuxostat, and a medicine having the composition of B below containing inosine were manufactured and put in the same bag separated to prevent mixing with each other for adjustment into one dose, i.e., a daily dose, thereof in the same box.

A. Febuxostat Tablet
  Febuxostat: 20 mg
  Alpha starch (disintegrating binder): 70 mg
  Silicified microcrystalline cellulose (filler): 32.656 mg
  Croscarmellose sodium (disintegrator): 10 mg
  Magnesium stearate (lubricant): 0.8 mg
B. Inosine
  Inosine: 0.5 g

INDUSTRIAL APPLICABILITY

Intracellular ATP was able to be enhanced by combined administration of allopurinol, topiroxostat, or febuxostat. This is a new pharmacological action different from conventional drugs. Therefore, the present invention is considered to be effective for various diseases having ATP reduction as a pathological condition.

Additionally, the uric acid value raising action of inosine was suppressed by the combined use with allopurinol, topiroxostat, or febuxostat. Therefore, for patients to which allopurinol, topiroxostat, or febuxostat is administered for treatment of hyperuricemia, ATP can be increased without decreasing the therapeutic effect on hyperuricemia.

The invention claimed is:

1. A method of enhancing intracellular ATP in human or animal, comprising the step of:
  administering to a human or an animal A) and B):
    A) allopurinol or topiroxostat, or a pharmaceutically acceptable salt thereof; and
    B) any one or more compounds selected from inosine, inosinic acid, and pharmaceutically acceptable salts thereof.

2. The method of enhancing intracellular ATP according to claim 1, wherein A) and B) are a combination drug including A) and B).

3. A method of enhancing intracellular ATP comprising the step of
  administering A) and B) to a patient with hemolytic anemia, ischemic heart disease, heart failure, amyotrophic lateral sclerosis, Parkinson's disease, or ADSL deficiency:
    A) allopurinol or topiroxostat, or a pharmaceutically acceptable salt thereof; and
    B) any one or more compounds selected from inosine, inosinic acid, and pharmaceutically acceptable salts thereof.

4. The method of claim 1 of enhancing intracellular ATP in the human, wherein the administering is to the human.

5. The method of claim 3, wherein the patient is a human.

6. The method of claim 1, wherein the administering is orally administering.

7. The method of claim 3, wherein the administering is orally administering.

8. The method of claim 1, wherein the allopurinol is about 50 to 800 mg/day of allopurinol, and wherein the topiroxostat is about 40 to 160 mg/day of topiroxostat.

9. The method of claim 1, wherein B) is 0.5 to 4.0 g/day of inosine.

10. The method of claim 3, wherein the allopurinol is about 50 to 800 mg/day of allopurinol and the topiroxostat is about 40 to 160 mg/day of topiroxostat.

11. The method of claim 3, wherein B) is 0.5 to 4.0 g/day of inosine.

* * * * *